United States Patent
Fulper et al.

(10) Patent No.: US 12,324,857 B2
(45) Date of Patent: Jun. 10, 2025

(54) APPARATUS AND PROCESS FOR SECONDARY ENCAPSULATION OF SOLID INCLUSIONS USING THE ROTARY DIE PROCESS

(71) Applicant: R.P. Scherer Technologies, LLC, Carson City, NV (US)

(72) Inventors: David Fulper, Clearwater, FL (US); Knight Arthur McGowan, Tampa, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 894 days.

(21) Appl. No.: 17/298,184

(22) PCT Filed: Nov. 27, 2019

(86) PCT No.: PCT/US2019/063538
§ 371 (c)(1),
(2) Date: May 28, 2021

(87) PCT Pub. No.: WO2020/112953
PCT Pub. Date: Jun. 4, 2020

(65) Prior Publication Data
US 2022/0096388 A1 Mar. 31, 2022

Related U.S. Application Data

(60) Provisional application No. 62/772,875, filed on Nov. 29, 2018.

(51) Int. Cl.
*A61K 9/48* (2006.01)
*B65B 3/00* (2006.01)
*B65B 3/02* (2006.01)
*B65B 47/04* (2006.01)

(52) U.S. Cl.
CPC ............ *A61K 9/4833* (2013.01); *B65B 3/003* (2013.01); *B65B 3/022* (2013.01); *B65B 47/04* (2013.01)

(58) Field of Classification Search
CPC ...... A61K 9/4833; B65B 3/003; B65B 3/022; B65B 47/04
See application file for complete search history.

(56) References Cited

U.S. PATENT DOCUMENTS

| | | | |
|---|---|---|---|
| 4,655,027 A | 4/1987 | Chasman | |
| 5,329,749 A | 7/1994 | Yamamoto et al. | |
| 2003/0014946 A1* | 1/2003 | Steele | B65B 9/042 53/454 |
| 2003/0019797 A1 | 1/2003 | Yamamoto et al. | |
| 2003/0059614 A1* | 3/2003 | Sadek | B30B 11/16 424/478 |
| 2015/0057304 A1 | 2/2015 | Thompson et al. | |
| 2015/0238429 A1* | 8/2015 | Fang | A61P 25/28 514/646 |
| 2017/0095425 A1 | 4/2017 | Altamar et al. | |

FOREIGN PATENT DOCUMENTS

| | | |
|---|---|---|
| EP | 2603900 A2 | 6/2013 |
| JP | 2000086502 A | 3/2000 |
| JP | 2001048809 A | 2/2001 |
| KR | 101268491 B1 | 6/2013 |
| WO | 0154645 A1 | 8/2001 |

OTHER PUBLICATIONS

Keck Cornelia M. et al., "Moderne Pharmazeutische Technologie", Jan. 1, 2009, URL:http://pharmazie-lehrbuch.de/Moderne%20Pharmazeutische%20Technologie.pdf, 118 Pages.
Supplementary European Search Report for EP Patent Application No. 19889330.7, dated Oct. 13, 2022, 19 pages.
International Search Report for International Application No. PCT/US2019/063538 mailed on Feb. 7, 2020, 2 pgs.
Extended European Search Report for European Application No. No. 19889330.7, mailed Apr. 5, 2023, 24 Pages.
Written Opinion for International Application No. PCT/US2019/063538, mailed Feb. 7, 2020, 7 Pages.

* cited by examiner

*Primary Examiner* — Snigdha Maewall
(74) *Attorney, Agent, or Firm* — Lowenstein Sandler LLP (57) ABSTRACT

Disclosed herein are a manufacturing process for encapsulating at least one solid inclusion into a softgel capsule. Also disclosed herein is a system for secondary encapsulation of solid inclusions using the rotary die process and system. Also disclosed herein are dosage forms having at least one solid inclusion encapsulated therein.

16 Claims, 4 Drawing Sheets

APPARATUS AND PROCESS FOR SECONDARY ENCAPSULATION OF SOLID INCLUSIONS USING THE ROTARY DIE PROCESS

CROSS-REFERENCE TO RELATED APPLICATIONS

This application is a national phase entry under 35 U.S.C. § 371 of International Application No. PCT/US2019/063538, filed on Nov. 27, 2019, which claims the benefit of priority of Patent Application No. 62/772,875, filed on Nov. 29, 2018. The contents of these applications are hereby incorporated by reference herein in their entirety.

FIELD OF THE INVENTION

The present invention relates generally to dosage forms for oral administration comprising at least one solid inclusion encapsulated therein, a manufacturing process, and a manufacturing apparatus or system therefor. More particularly, the present invention relates to secondary encapsulation of at least one solid inclusion.

BACKGROUND OF THE INVENTION

The ability to incorporate two or more active ingredients in a single dosage form offers several advantages. The advantages include convenient delivery of multiple medications, avoidance of potential mistakes by a user if many medications are to be taken individually and at the same time, increased user compliance, possible synergistic effect, and possible controlled delivery.

Various oral medications have been manufactured in the form of softgel capsules. A liquid or semi-solid fill composition is typically encapsulated in softgel capsules using the conventional rotary die method. However, the incorporation of two or more active ingredients in a softgel capsule can result in chemical incompatibilities or reactions between the different active ingredients.

Attempts have been made to separate active ingredients to avoid chemical incompatibilities and to maintain the chemical stability of the different active ingredients. Physical barriers may be utilized to separate fill formulations containing different active ingredients. For example, a gelatin partition may be used to divide a softgel capsule into separate chambers with each chamber containing a different fill formulation.

Further attempts have been made to incorporate two or more active ingredients by formulating the fill formulations so that they form different liquid phases or are incompatible. For example, two different fill formulations forming different liquid phases may be layered side-by-side in a softgel capsule. The use of hydrophobic and hydrophilic fill formulations allows for the fill formulations to be layered side-by-side in a softgel capsule. Softgel capsule fill formulations may also be formulated to incorporate active ingredient particles suspended in a liquid carrier.

Preformed solid dosage forms may be enrobed with a gelatin coating to permit easier swallowing of the dosage form. Enrobed solid dosage forms may incorporate a second active ingredient in the gelatin coating.

There exists a need for dosage forms capable of providing single ingestion of multiple dosage forms. It is desirable to provide dosage forms containing at least one solid inclusion and optionally a liquid fill phase which maintains the chemical stability of each inclusion (solid and/or liquid) and prevents any chemical reaction between the multiple inclusions. It is also desirable to incorporate preformed solid inclusions to retain the established pharmaceutical characteristics of the preformed inclusions (optionally in combination with a liquid phase) such as physical and chemical stability, active ingredient release profile of the solid inclusion, bioavailability and clinical performance.

OBJECTS AND SUMMARY OF THE INVENTION

It is an object of certain embodiments of the present invention to provide an apparatus compatible with the rotary die encapsulation process for encapsulating solid inclusions in soft elastic capsules.

It is another object of certain embodiments of the present invention to provide a method for encapsulating solid inclusions in soft elastic capsules.

It is a further object of certain embodiments of the present invention to provide a dosage form in the form of a capsule that encapsulates a preformed solid inclusion.

The above objects of the present invention and others may be achieved by the present invention which in some embodiments is directed to a method for secondary encapsulation of solid inclusions using a rotary die process, to an apparatus for secondary encapsulation of solid inclusions using a rotary die process, and/or to a dosage form comprising at least one solid inclusion encapsulated in a capsule prepared according to any of the methods or with the systems (apparatuses) disclosed herein.

In one embodiment, the method may comprise introducing a continuous first film on a first rotating encapsulation die comprised of a first series of cavities. The method may further comprise introducing a continuous second film on a second rotating encapsulation die comprises of a second series of cavities. The first series of die cavities and the second series of die cavities may be synchronized to align with each other as the first rotating encapsulation die and the second rotating encapsulation die turn such that each cavity in the first series of cavities and in the second series of cavities may form one half of a total cavity for a capsule to be formed. The method may further comprise mechanically dispensing at least one solid inclusion from a dispensing tube. The dispensing tube may be integrated into a wedge positioned between the continuous first film and the continuous second film of the first rotating encapsulation die and of the second rotating encapsulation die, respectively. The dispensing tube may be positioned off-center in the wedge and aligned with a first row of cavities in the first rotating encapsulation die and a second row of cavities in the second rotating encapsulation die. The method may further comprise trapping the at least one solid inclusion between the continuous first film, in a section of the continuous first film aligned over a die cavity, and the wedge to form a first half of a capsule within a cavity of the first rotating encapsulation die. The method may further comprise rotating the first rotating encapsulation die and the second rotating encapsulation die in counter directions to contact the continuous first film and the continuous second film between the first rotating encapsulation die and the second rotating encapsulation die to form a close capsule. The method may further comprise simultaneously fusing a first pair of edges of the continuous first film and a second pair of edges of the continuous second film between the walls of the cavity of the first rotating encapsulation die and a cavity wall of the second rotating encapsulation die to hermetically seal the at least one solid inclusion into the closed capsule.

In one embodiment, the system for secondary encapsulation of at least one solid inclusion in a capsule may comprise a first rotating encapsulation die comprising a first set of die cavities and a second rotating encapsulation die comprising a second set of die cavities. The apparatus may further comprise a continuous first film on the first rotating encapsulation die and a continuous second film on the second rotating encapsulation die. The apparatus may further comprise a wedge between the first rotating encapsulation and the second rotating encapsulation die. The apparatus may further comprise a dispensing tube integrated into the wedge and positioned off-center in the wedge such that the dispensing tube is aligned with a first row of cavities in the first rotating encapsulation die and with a second row of cavities in the second rotating encapsulation die for dispensing at least one solid inclusion. The apparatus may further comprise a mechanical dispensing mechanism and a synchronization mechanism for synchronizing the rotating of at least one of the first rotating encapsulation die or the second rotating encapsulation die with the mechanical dispensing of the at least one solid inclusion such that the at least one solid inclusion is timely trapped between the continuous first film and the wedge in a cavity within the first set of die cavities to form a first half of a capsule.

Mechanically dispensing at least one solid inclusion may be performed through various mechanical dispensing mechanisms, such as, with a dispensing plunger, with an actuator (e.g., electromagnetic, rotary screw driven, cam driven, hydraulically driven, pneumatically driven and so on), with a pump in a batch configuration, with a pump in a continuous or semi-continuous configuration and so on.

In one embodiment, a dosage form prepared according to the methods described herein and/or with the system described herein is disclosed. The dosage form may encapsulate at least one solid inclusion (e.g., beads, tablets, capsules, caplets, pellets, granules, and so on). The solid inclusion may be pre-formed and could have different shapes (e.g., round, oval, oblong, spherical and so on).

BRIEF DESCRIPTION OF THE DRAWINGS

The above and other features of the present disclosure, their nature, and various advantages will become more apparent upon consideration of the following detailed description, taken in conjunction with the accompanying drawings, in which.

DEFINITIONS

As used herein, the singular forms "a," "an," and "the" include plural references unless the context clearly indicates otherwise. Thus, for example, reference to "a solid inclusion" includes a single solid inclusion as well as a mixture of two or more identical or different solid inclusions, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±10%, such that "about 10" would include from 9 to 11.

As used herein, the terms "active agent," "active ingredient," "active pharmaceutical ingredient," "API," and "drug" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, complexes, stereoisomers, crystalline forms, co-crystals, ether, esters, hydrates, solvates, and mixtures thereof, where the form is pharmaceutically active. In certain embodiment, the term "active ingredient" may refer to a material intended to produce a cosmetic effect (with or without a therapeutic effect), whether or not approved by a government agency for that purpose.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

The terms "softgel capsule" and "soft elastic capsule" may be used interchangeably herein.

DETAILED DESCRIPTION

The present invention is directed to the secondary encapsulation of at least one solid inclusion using a rotary die process. An apparatus and process for manufacturing dosage forms capable of encapsulating at least one solid inclusion and optionally a liquid fill are disclosed. In dosage forms that encapsulate at least one solid inclusion and a liquid fill, the solid phase and the liquid phase may be independently introduced into the dosage form. The at least one solid inclusion and the liquid fill (if present) may contain active ingredients including APIs, nutritional supplements, or substances for therapeutic or cosmetic (e.g., non-pharmacologic action) purposes.

The dosage forms of the present invention are capable of delivering multiple medications or therapeutic substances in a single dose. The dosage forms of the present invention may be formulated to provide different or identical release profiles for the various medications or therapeutic substances therein. Exemplary release profiles may include, without limitations, immediate release, extended release, delayed release and so on. The secondary encapsulation of at least one solid inclusion in dosage forms disclosed herein permits retention of established pharmaceutical characteristics of the solid inclusion and of the liquid fill (if present).

Figure 1:
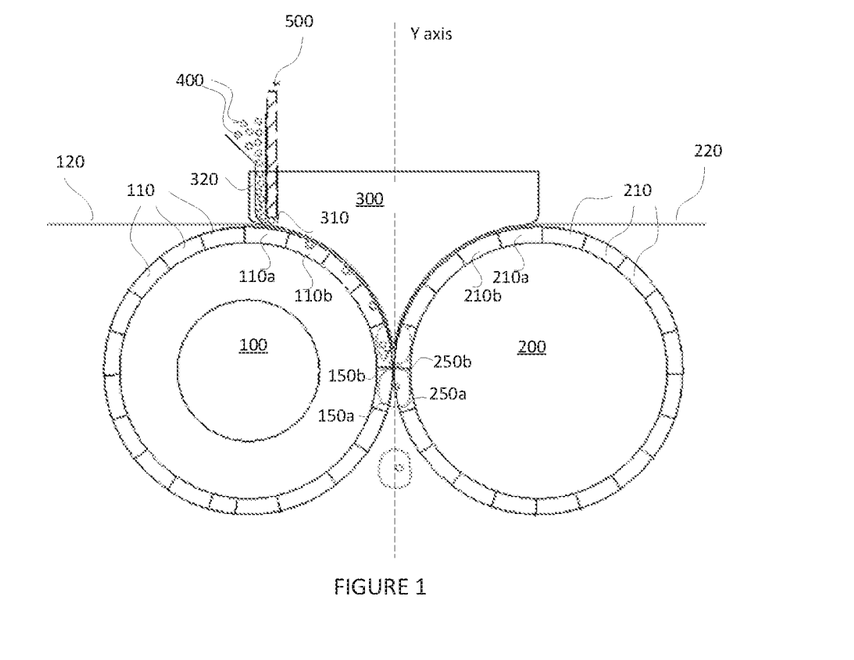
FIG. 1 illustrates a rotary die configuration according to embodiments disclosed herein.

FIG. 1 illustrates an apparatus or system for manufacturing a dosage form containing at least one solid inclusion. FIG. 1 depicts a rotary die configuration according to embodiments disclosed herein. The system may comprise a first rotating encapsulation die 100 and a second rotating encapsulation die 200. The first rotating encapsulation die 100 may comprise a first set of die cavities 110. The second rotating encapsulation die 200 may comprise a second set of die cavities 210. A first continuous film 120 and a second continuous film 220 may be formed on a first and a second drum, respectively (not shown in the figure), and then threaded over the first rotating encapsulation die 100 and over the second rotating encapsulation die 200, respectively.

The system may further comprise a wedge 300 positioned between the first rotating encapsulation die 100 and the second rotating encapsulation die 200. A dispensing tube 310 may be integrated into the wedge 300 and positioned off-center in the wedge 300. The center of the wedge in FIG. 1 is depicted along vertical axis Y. Dispensing tube 310 may be aligned with a first row of cavities 110a in the first rotating encapsulation die 100 and a second row of cavities 210a in the second rotating encapsulation die 200. Feed tube 320 may comprise a plurality of solid inclusions 400 in some embodiments. Dispensing tube 310 may be positioned so as to dispense at least one solid inclusion 400 between the wedge 300 and the first continuous film 120 precisely over a cavity in the first set of die cavities 110. Such precise dispensing will allow the at least one solid inclusion 400 to become trapped between the first continuous film 120 and the wedge 300 in a section of the first continuous film 120 that is aligned over a die cavity in the first set of die cavities 110, thereby forming a first half of a capsule within a cavity of the first rotating encapsulation die 100.

The precise dispensing may be controlled through a mechanical dispensing mechanism for the solid inclusion and a synchronization mechanism. The synchronization mechanism may be useful for synchronizing the rotation of at least one of the first rotating encapsulation die 100 or the second rotating encapsulation die 200 with the mechanical dispensing of the solid inclusion 400 such that at least one solid inclusion 400 is timely trapped between the first continuous film 120 and the wedge 300 in a section of the first continuous film 120 that is aligned over a die cavity in the first set of die cavities 110, thereby forming a first half of a capsule. Synchronization may be attained via mechanical means such as, without limitations, gears that maintain a mechanical linkage between the dispenser and the rotating encapsulation dies, or by means of encoding device that could track the position of the encapsulation dies and signals the dispenser, or a combination thereof.

Although the description of the system and FIG. 1 depict a single dispensing tube 310 aligned with the first row of cavities 110a, the instant disclosure also encompasses the presence of additional dispensing tube(s) (not shown) that may be aligned with the second row of cavities 210a and/or with other cavities, e.g., 110b, 210b and so on. It should be understood that the presence of additional dispensing tube(s) may be a way for including more solid inclusions in a single capsule. Each additional dispensing tube may comprise a plurality of solid inclusions in some embodiments. Each additional dispensing tube may be positioned so as to dispense at least one solid inclusion between the wedge 300 and at least one of the first continuous film 120 or the second continuous film 220 (depending on the positioning of the dispensing tube) precisely over a cavity in the first set of dies cavities 110 or in the second set of die cavities 210 (depending on the positioning of the dispensing tube). Such precise dispensing will allow the at least one solid inclusion from the additional dispensing tube(s) to become trapped between the first continuous film 120 or the second continuous film 220 and the wedge 300 in a section of the first continuous film 120 or the second continuous film 220 that is aligned over a die cavity in the first set of die cavities 110 or in the second set of die cavities 210, thereby forming a half of a capsule within a cavity of the first rotating encapsulation die 100 or within a cavity of the second rotating encapsulation die 200, respectively.

The precise dispensing from each additional dispensing tube(s) may be controlled through a mechanical dispensing mechanism for the solid inclusion and a synchronization mechanism. The synchronization mechanism may be useful for synchronizing the rotation of at least one of the first rotating encapsulation die 100 or the second rotating encapsulation die 200 with the mechanical dispensing of the solid inclusion from each additional dispensing tube(s) such that said at least one solid inclusion gets timely trapped between the first continuous film 120 or the second continuous film 220 and the wedge 300 in a section of the first continuous film 120 or of the second continuous film 220 that is aligned over a die cavity in the first set of die cavities 110 or in the second set of die cavities 210, respectively, thereby forming a half of a capsule. Synchronization may be attained via mechanical means such as, without limitations, gears that maintain a mechanical linkage between the dispenser and the rotating encapsulation dies, or by means of encoding device that could track the position of the encapsulation dies and signals the dispenser, or a combination thereof.

In some embodiments where there is more than one dispensing tube, the at least one solid inclusion in the first dispensing tube may comprise one type of API, nutritional supplement or substance used for therapeutic or cosmetic (e.g., non-pharmacologic action) purposes. The at least one solid inclusion in each additional dispensing tube(s) may be an identical API, nutritional supplement or substance used for therapeutic or cosmetic (e.g., non-pharmacologic action) purposes as in the first dispensing tube. Alternatively, the at least one solid inclusion in each additional dispensing tube(s) may be a different API, nutritional supplement or substance used for therapeutic or cosmetic (e.g., non-pharmacologic action) purposes from the solid inclusions in the first dispensing tube.

The solid inclusions may be selected from the group consisting of beads, tablets, capsules, caplets, pellets, granules, and combinations thereof. In one embodiment, the solid inclusions are beads. In one embodiment, the solid inclusions are tablets. In one embodiment, the solid inclusions are capsules. In one embodiment, the solid inclusions are caplets. In one embodiment, the solid inclusions are pellets. In one embodiment, the solid inclusions are granules. In certain embodiments, the solid inclusion may comprise another suitable dosage form.

The solid inclusions may have a shape selected from the group consisting of round, oval, oblong, and spherical. In one embodiment, the solid inclusions are round. In one embodiment, the solid inclusions are oval. In one embodiment, the solid inclusions are oblong. In one embodiment, the solid inclusions are spherical. Spherical solid inclusions may have a circularity ranging from about 0.7 to about 1, from about 0.8 to about 1, or from about 0.9 to about 1. In certain embodiments, the solid inclusions may comprise other suitable shapes.

Returning to the FIG. 1, one mechanical dispensing mechanism may be dispensing plunger 500 placed inside the dispensing tube 310. The dispensing tube 310 may be positioned adjacent to a feeding tube 320. The feeding tube 320 may comprise a plurality of solid inclusions 400 in certain embodiments. Solid inclusions 400 may flow down feeding tube 320 through gravity. As dispensing plunger 500 gets retracted, the at least one solid inclusion 400 may be transferred from feeding tube 320 into dispensing tube 310. As the first rotating encapsulation die 100 (and as the second rotating encapsulation die 200) turn, dispensing plunger 500 is timed to eject the at least one solid inclusion out of the dispensing tube 310 and trap it between the first continuous film 120 and the wedge 300 in a section of the first continuous film 120 that is aligned over a die cavity in the first set of die cavities 110. The dispensing plunger 500 may assist in controlling the timing for ejecting the at least one solid inclusion and in controlling the number of solid inclusions that get ejected into each half capsule.

Although not depicted in FIG. 1, a similar dispensing system may be configured on the second rotating encapsulation die 200.

The system depicted in FIG. 1 may be used in some embodiments in a method for forming secondary encapsulation of solid inclusions. The method may comprise forming a continuous first film 120 on a first drum (not shown) and threading continuous first film 120 over first rotating encapsulation die 100 comprised of a first series of cavities 110. The method may further comprise forming a continuous second film 220 on a second drum (not shown) and threading the continuous second film 220 over a second rotating encapsulation die 200 comprised of a second series of dies cavities 210. The first series of dies cavities 110 and the second series of die cavities 210 may be synchronized to align with each other as the first rotating encapsulation die 100 and the second rotating encapsulation die 200 turn. Each cavity in the first series of die cavities 110 and in the second series of die cavities 210 may form one half of a total cavity for a capsule to be formed.

The method may further comprise mechanically dispensing at least one solid inclusion 400 from a dispensing tube 310. The dispensing tube 310 may be integrated into a wedge 300 positioned between the continuous first film 120 and the continuous second film 220 of the first rotating encapsulation die 100 and of the second rotating encapsulation die 200, respectively. The dispensing tube 310 may be positioned off-center (the center being depicted by the Y axis) in the wedge 300. The dispensing tube 310 may be aligned with a first row of cavities 110a in the first rotating encapsulation die 100 and a second row of cavities 210a in the second rotating encapsulation die 200.

The method may further comprise trapping the at least one solid inclusion 400 between the continuous first film 120, in a section of the continuous first film 120 aligned over a die cavity, and the wedge 300 to form a first half of a capsule within a cavity of the first rotating encapsulation die 100.

The method may further comprise rotating the first rotating encapsulation die 100 and the second rotating encapsulation die 200 in counter directions to contact the continuous first film 120 and the continuous second film 220 between the first rotating encapsulation die 100 and the second rotating encapsulation die 200 to form a closed capsule. The method may further comprise, simultaneously with the rotating, fusing a first pair of edges (150a and 150b) of continuous first film 120 and a second pair of edges (250a and 250b) of continuous second film 220 between the cavity wall of the first rotating encapsulation die 100 and a cavity wall of the second rotating encapsulation die 200 to hermetically seal the at least one solid inclusion into the closed capsule.

In some embodiments where the mechanical dispensing mechanism comprises a dispensing plunger 500 placed inside a dispensing tube 310, with the dispensing tube 310 being positioned adjacent to a feeding tube 320 that contains the at least one solid inclusion 400, as depicted in FIG. 1, the mechanically dispensing at least one solid inclusion may comprise the following actions. Mechanically dispensing the at least one solid inclusion 400 may comprise retracting a dispensing plunger 500 in the dispensing tube 310. In some embodiments, retracting the dispensing plunger 500 may result in the at least one solid inclusion 400 being transferred from a feeding tube 320 into the dispensing tube 310. In other embodiments, mechanically dispensing the at least one solid inclusion 400 may further comprise transferring the at least one solid inclusion from the feeding tube 320 into the dispensing tube 310. Mechanically dispensing the at least one solid inclusion 400 may further comprise timing the dispensing plunger 500 to eject the at least one solid inclusion 400 from the dispensing tube 310 with the rotating of the first rotating encapsulation die 100 such that at least one solid inclusion is trapped between the continuous first film 120 and the wedge 300 in the cavity of the first rotating encapsulation die 100 to form a first half of a capsule. Mechanically dispensing the at least one solid inclusion 400 may further comprise ejecting the at least one solid inclusion.

In some embodiments, the system for secondary encapsulation of the at least one solid inclusion may further comprise a liquid fill or a semi-solid fill dispensing tube integrated into a center of the wedge. The liquid fill or semi-solid fill dispensing tube may be used for mechanically dispensing and filling the capsule with the liquid fill or with the semi-solid fill in synchrony with the rotation of at least one of the first rotating encapsulation die or the second rotating encapsulation die to allow for timely trapping of the dispensed liquid fill or the dispensed semi-solid fill with the at least one solid inclusion within the capsule.

In embodiments where the system includes a dispensing tube for a liquid fill or a semi-solid fill, the method for secondary encapsulation may further comprise mechanically dispensing a liquid through the wedge (or through the liquid fill or semi-solid fill dispensing tube) in synchrony with the rotating of the first rotating encapsulation die 100 and of the second rotating encapsulation die 200 to allow for timely trapping the dispensed liquid (or the dispensed semi-solid fill) with the solid inclusion within the closed capsule.

Figures 2A, 2B, 2C:
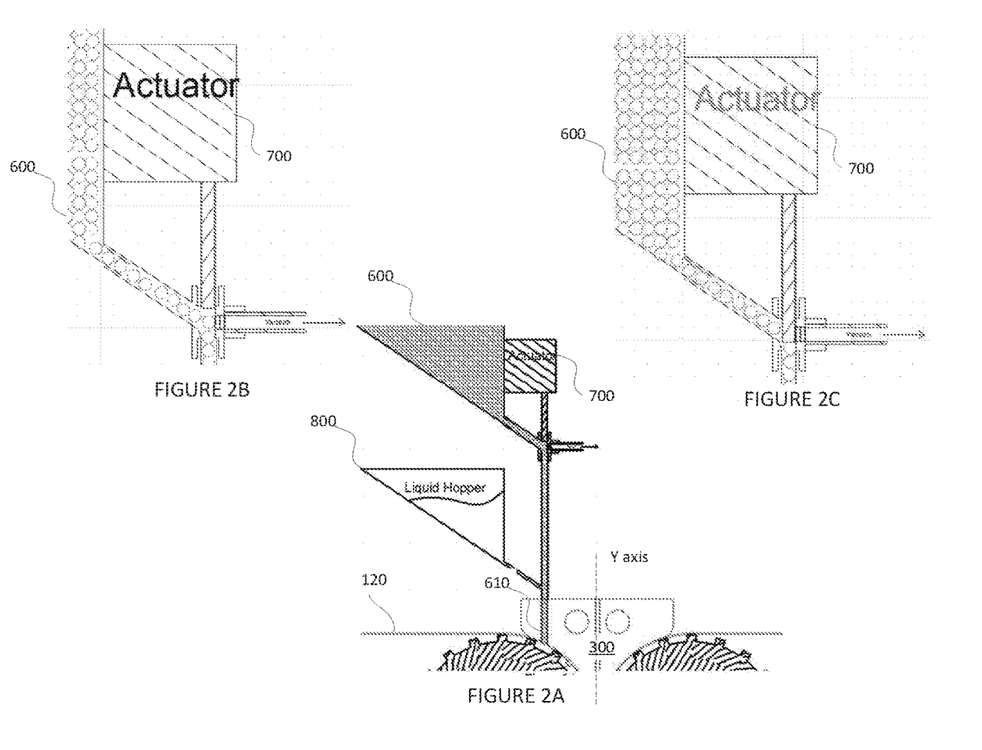
FIGS. 2A-2C illustrate a mechanical dispensing mechanism employing an actuator according to embodiments disclosed herein and its operation mode.

FIGS. 2A-2C illustrate a mechanical dispensing mechanism employing an actuator according to embodiments disclosed herein and its operation mode. Specifically, FIG. 2A depicts a hopper 600 for holding a reservoir of inclusions 400 (such as those depicted in FIG. 1). Hopper 600 may be connected to a dispensing tube 610 and may be positioned above the dispensing tube. Dispensing tube 610 may be integrated into the wedge 300 and positioned off-center in the wedge 300. The center of the wedge in FIG. 2A is depicted along vertical axis Y. Dispensing tube 610 may be aligned with a first row of cavities 110a in the first rotating encapsulation die 100 and a second row of cavities 210a in the second rotating encapsulation die 200, similar to the positioning of dispensing tube 310 in FIG. 1.

Dispensing tube 610 may be connected to an actuator 700 positioned at the top of the dispensing tube. Actuator 700 may be used for loading the dispensing tube 610 and ejecting the at least one solid inclusion 400 in synchrony with the rotation of at least one of the first rotating encapsulation die 100 or the second rotating encapsulation die 200 such that the at least one solid inclusion gets trapped between at least one of the continuous first film 120 or the continuous second film 220 and the wedge 300 in a cavity within at least one of the first set of die cavities 100 or the second set of die cavities 200, respectively, to form a first half of a capsule.

Exemplary modes of operation of actuator 700 are better depicted in the blown up views of FIGS. 2B and 2C. FIG. 2B depicts a loading process of the solid inclusions 400 from hopper 600 into dispensing tube 610. Specifically, the loading of the at least one solid inclusion 400 from the hopper 600 into the dispensing tube 610 occurs when the actuator 700 is in a retracted position as seen in FIG. 2B. FIG. 2C depicts an ejection process of the solid inclusions 400 from dispensing tube 610 into a cavity of the first encapsulation die 100 to be trapped between the continuous first film 120 and wedge 300. Specifically, the ejection process of the solid inclusion 400 from dispensing tube 610 occurs when actuator 700 extends as seen in FIG. 2C. Actuator 700 may extend a distance equivalent to the number of solid inclusions 400 desired to be placed into the capsule (or into a first half of a capsule). For instance, the actuator may extend a distance x for one solid inclusion, a distance 2x for two solid inclusions, a distance 3x for three solid inclusions and so on. Upon extension of the actuator 700, the desired number of solid inclusions may be moved into the capsule as a consequence of their adjacent contact chain to inclusions adjacent to the actuator.

Actuator 700 may be any number of linear actuators with sufficient distance control to dispense the desired number of inclusions at a speed sufficient to match the dwell of the die pocket cavity under the injection orifice at the bottom of the dispensing tube. Suitable actuators may be selected from the group consisting of electromagnetic, rotary screw driven, cam driven, hydraulically driven, vacuum driven, and pneumatically driven. Regardless of the selected actuator as a mechanical dispensing mechanism, the means of actuation may be synchronized with the rotation of the rotating encapsulation dies and the series of die cavities therein.

In the mechanical dispensing mechanism of FIG. 2A, a liquid hopper 800 may also be present. Liquid hopper 800 may be used to supply liquid into dispensing tube 610 to displace air that could otherwise manifest as air bubbles in the capsule. With the liquid hopper configuration shown in FIG. 2A, dispensing tube 610 may be filled with liquid to a level equivalent to the level of liquid in hopper 800 through hydrostatic pressure. The configuration depicted in FIG. 2A should not be construed as limiting. Alternative schemes, such as pumping systems that recirculate fluid into and out of the dispensing tube through a "T" connection for instance, may also be suitable.

Supplying liquid into the dispensing tube to displace air that could otherwise manifest as air bubbles in the capsule may result in a closed capsule that comprises less than about 5 wt % air, less than about 4 wt % air, less than about 3 wt % air, less than about 2 wt % air, less than about 1 wt % air, less than about 0.5 wt % air, less than about 0.1 wt % air, less than about 0.01 wt % air, substantially no air, or no air at all.

In some embodiments where the mechanical dispensing mechanism comprises an actuator 700 as depicted in FIGS. 2A-2C, the mechanically dispensing at least one solid inclusion may comprise the following actions. Mechanically dispensing at least one solid inclusion may comprise retracting an actuator 700 positioned at a top of a dispensing tube 610 to load a plurality of solid inclusions 400 into the dispensing tube 610 from a hopper 600 holding a reservoir of solid inclusions 400. Mechanically dispensing at least one solid inclusion may further comprise timing the actuator to extend and eject the at least one solid inclusion 400 from dispensing tube 610 in synchrony with the rotation of the first rotating encapsulation die 100 such that the at least one solid inclusion 400 may get trapped between the continuous first film 120 and the wedge 300 in the cavity of the first rotating encapsulation die 100 to form a first half of a capsule. Mechanically dispensing at least one solid inclusion may further comprise extending the actuator a distance equivalent to a number of solid inclusions to be placed in the capsule (e.g., a distance x for one solid inclusion, a distance 2x for two solid inclusions, a distance 3x for three solid inclusions and so on). Mechanically dispensing at least one solid inclusion may further comprise ejecting the number of solid inclusions to be placed in the capsule.

Although not depicted in FIGS. 2A-2C, a similar dispensing system that utilizes an actuator may be configured on the second rotating encapsulation die 200.

Figure 3:
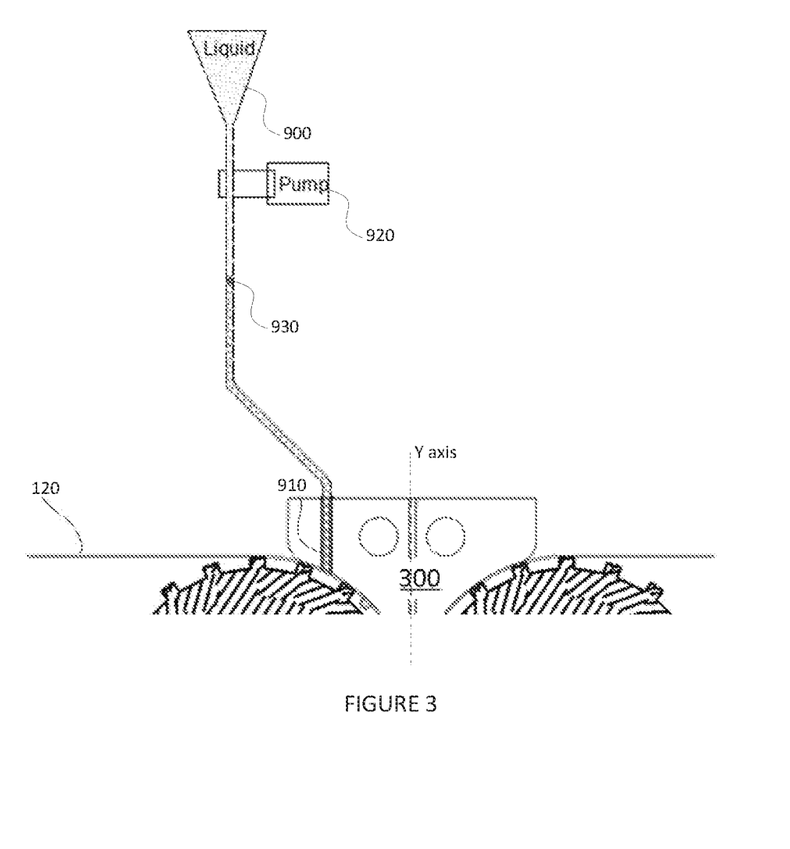
FIG. 3 illustrates a mechanical dispensing mechanism employing a pump according to embodiments disclosed herein.

FIG. 3 illustrates a mechanical dispensing mechanism employing a pump according to embodiments disclosed herein. Specifically, FIG. 3 depicts a dispensing tube 910 holding a plurality of solid inclusions 400 and a liquid hopper 900 placed at the top end of dispensing tube 910. Dispensing tube 910 and liquid hopper 900 may be connected to a pump 920 for dispensing the at least one solid inclusion in synchrony with the rotation of at least one of the first rotating encapsulation die 100 or the second rotating encapsulation die 200 such that at least one solid inclusion 400 gets trapped between at least one of the continuous first film 120 or the continuous second film 220 and the wedge 300 in a cavity within at least one of the first set of die cavities 110 or the second set of die cavities 210 to form a first half of a capsule.

Liquid hopper 900 may comprise any suitable liquid to be placed above solid inclusions 400. The fit of the solid inclusions 400 in dispensing tube 910 will determine in part how much volume should be pumped to force the sold inclusions into the die cavities (or die pockets). With a more loosely fitted solid inclusions, more fluid slippage may occur in dispensing tube 910 as compared to solid inclusions that are more tightly fitted. To reduce or eliminate fluid slippage, the liquid may be separated from the solid inclusions with a special tight fitting inclusion 930 that may act as a seal to minimize slippage of fluid. Such an arrangement may result in a more accurate and precise dispensing of the desired number of solid inclusions into a die cavity (or die pocket).

An alternative solution for controlling fluid slippage past the solid inclusions may be by adjusting the flow properties of the fluid supplied from the liquid hopper. For instance, by increasing the viscosity of the fluid or by formulating the fluid to have plug flow properties in the dispensing tube 910, fluid slippage may also be minimized.

Pump 920 may be chosen from a variety of positive displacement pumps that provide sufficient accuracy and precision to deliver the volume required to dispense the desired number of solid inclusions to the die cavity (or die pocket).

In some embodiments where the mechanical dispensing mechanism comprises a pump configuration as depicted in FIG. 3, the mechanically dispensing at least one solid inclusion may comprise the following actions. Mechanically dispensing at least one solid inclusion may comprise loading solid inclusions into dispensing tube 910 with the dispensing tube comprising a liquid above the solid inclusions and being connected to pump 920. Mechanically dispensing at least one solid inclusion may further comprise actuating pump 920 in synchrony with the rotation of the first rotating encapsulation die 100 such that the at least one solid inclusion 400 may get trapped between the continuous first film 120 and the wedge 300 in the cavity of the first rotating encapsulation die 100 to form a first half of a capsule. Mechanically dispensing at least one solid inclusion may further comprise pumping a volume of liquid into dispensing tube 910 that is equivalent to the number of solid inclusions desired to be placed into the capsule. In other words, the pump actuates in synchrony with the die pockets to pump a specific volume of liquid into the dispensing tube to force the solid inclusions into the die cavities (or die pockets). Mechanically dispensing at least one solid inclusion may further comprise ejecting the number of solid inclusions to be placed in the capsule.

The configuration of FIG. 3 may be more suitable for smaller batches that require a limited number of solid inclusions that would allow manual loading of dispensing tube 910. Larger batches may benefit from a continuous loading mechanism described in more detail in FIGS. 4A-4B.

Figure 4A:
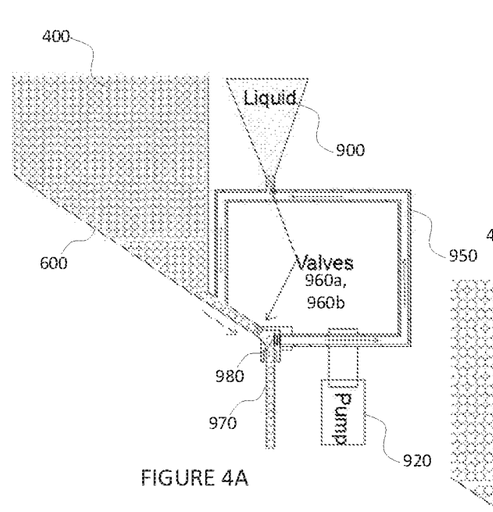
FIGS. 4A-4B illustrate a mechanical dispensing mechanism employing a pump in a continuous processing configuration according to embodiments disclosed herein.
Figure 4B:
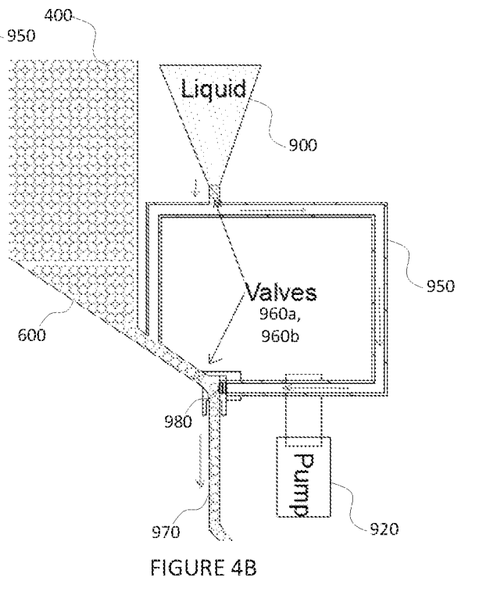

In FIGS. 4A-4B, pump 920 may be plumbed into a loop 950 with two unidirectional valves (960a, 960b). The flow pattern may be counter-clockwise, as illustrated in FIG. 4A, or clockwise as illustrated in FIG. 4B. In FIG. 4A (with a counter-clockwise flow pattern), at least one solid inclusion 400 may be drawn from hopper 600 into dispensing tube 970, where a screen 980 may prevent the at least one solid inclusion from entering the loop. In FIG. 4B (with a clockwise flow pattern), the at least one solid inclusion is forced down dispensing tube 970 into wedge 300 (not shown). The unidirectional valves (960a, 960b) prevent the flow of the at least one solid inclusion 400 back into hopper 600. Additional valves (not shown) may optionally be included to increase the robustness of the system. It should also be understood that the embodiments illustrated in the figures are exemplary and various other means of loading the dispensing tubes with the solid inclusions on a continuous or a semi-continuous basis are also possible.

All of the mechanical dispensing mechanisms disclosed herein provide the added advantage of accurately and precisely controlling the composition of the capsule content (e.g., the number of solid inclusions in each capsule, the timing and precise placement of each solid inclusion in the capsule, the volume of liquid in each capsule (if added), the exclusion of air content in each capsule and so on).

All the method steps described herein may be repeated to form a plurality of closed capsules encapsulating at least one solid inclusion. Thus, the methods described herein may further comprise repeating the mechanically dispensing (of solid inclusions and/or liquid fill and/or semi-solid fill), the trapping, the rotating, and the sealing to form a plurality of capsules, where each of the plurality of capsules may encapsulate at least one solid inclusion.

The present invention may also be directed to a dosage form comprising at least one solid inclusion prepared according to any of the methods and/or with any of the systems disclosed herein.

The shape and size of the final closed capsules can vary in accordance with the invention. The shape of the capsule may be, but is not limited to, round, oval, oblong, or a non-standard shape. Typical capsule dosage form shapes and sizes may be, but are not limited to, those as shown in Table 1. The invention provides the capability to incorporate into the closed capsule a wide range of solid inclusions (form and shape) to manufacture an infinite variety of softgel capsule shapes and sizes.

TABLE 1

Nominal Softgel Capsule Shapes and Sizes

| Nominal Size | Oblong Shape | | Oval Shape | |
|---|---|---|---|---|
| | Minimum Volume (ml) | Maximum Volume (ml) | Minimum Volume (ml) | Maximum Volume (ml) |
| 1 | 0.03 | 0.08 | 0.03 | 0.06 |
| 2 | 0.08 | 0.14 | 0.06 | 0.09 |
| 3 | 0.14 | 0.20 | 0.11 | 0.17 |
| 4 | 0.20 | 0.30 | 0.15 | 0.22 |
| 5 | 0.26 | 0.37 | 0.23 | 0.30 |
| 6 | 0.32 | 0.46 | 0.26 | 0.38 |
| 8 | 0.43 | 0.63 | 0.33 | 0.48 |
| 10 | 0.53 | 0.76 | 0.42 | 0.60 |
| 12 | 0.64 | 0.93 | 0.50 | 0.73 |
| 14 | 0.75 | 1.06 | 0.60 | 0.85 |
| 16 | 0.85 | 1.23 | 0.70 | 1.00 |
| 18 | 0.96 | 1.40 | 0.76 | 1.10 |
| 20 | 1.10 | 1.55 | 0.85 | 1.20 |
| 22 | 1.20 | 1.70 | 0.95 | 1.35 |
| 24 | 1.30 | 1.85 | 1.05 | 1.46 |
| 26 | 1.40 | 2.00 | 1.13 | 1.60 |
| 28 | 1.50 | 2.15 | 1.23 | 1.70 |
| 30 | 1.65 | 2.30 | 1.30 | 1.85 |

The solid inclusions encapsulated in the capsule may be selected from the group consisting of beads, tablets, capsules, caplets, pellets, granules, and combinations thereof. In some embodiments, other dosage forms may also be suitable as solid inclusions encapsulated in the capsules described herein. The solid inclusions may have a shape selected from the group consisting of round, oval, oblong, and spherical. Spherical solid inclusions may have a circularity ranging from about 0.7 to about 1, from about 0.8 to about 1, or from about 0.9 to about 1. In some embodiments, other shapes may also be suitable for the instant disclosure.

The solid inclusions encapsulated in the capsule may comprise preformed solid dosage form, such as a pharmaceutical finished dosage form suitable for administration to human or animal subject.

A preformed solid inclusion may be coated with one or more coatings, including but not limited to, immediate release coatings, protective coatings, enteric or delayed release coatings, sustained release coatings, barrier coatings, moisture shield coatings and combinations thereof. The one or more coatings on the solid inclusions are useful to provide controlled release of an active ingredient in the solid inclusion, protect the solid inclusion from interactions with other components in the capsule, or deliver one or more active ingredients from the solid inclusion with at a particular release profile.

The shell of the capsule (e.g., soft gelatin capsule) may be formed from plasticized gelatin or other functional polymeric materials that are typically used for encapsulation of liquids, fluids, pastes or other fill materials.

The outer shell of the capsule may be coated with one or more coatings, including but not limited to, immediate release coatings, protective coatings, enteric or delayed release coatings, sustained release coating, barrier coatings, and combinations thereof. The one or more coatings on the outer shell of the capsule may be useful to provide controlled release of the capsule, protect the shell from degradation, or deliver one or more active ingredients in the dosage form. Alternatively, additives such as pectin or synthetic polymers may be incorporated into the capsule shell to slow or target the dissolution on ingestion. The one or more coatings on the outer shell of the softgel capsule may be applied by any conventional technique, including but not limited to, pan coating, fluid bed coating or spray coating.

The liquid fill or semi-solid fill of the capsule (if present) may comprise one or more liquids or semi-solids that are compatible with the capsule shell and do not interfere with or degrade the solid inclusion. The liquid fill or semi-solid fill may comprise one or more combinations of fluids that may be broadly categorized as hydrophilic or lipophilic.

A lipophilic liquid fill or semi-solid fill may be an oil form of an active ingredient, an active ingredient or multiple active ingredients preparation that may be solutions, suspensions, emulsions, micro-emulsions, self-emulsifying systems, gels, and other liquids or semi-solids that will be known to those who are expert in the field of capsule formulations. Examples of useful oils include omega-3 fatty acids triglycerides (e.g., alpha-linolenic acid, eicosapentaenoic acid and docosahexaenoic acid), ethyl esters, vegetable oils, mineral oils or other food grade oil. Vegetable oils may include castor bean oil, coconut oil, peanut oil, palm kernel oil, canola oil, avocado oil, evening primrose oil, rice bran oil, borage oil, sunflower oil, soybean oil, palm oil, corn oil and safflower oil.

Hydrophilic liquid fill or semi-solid fill are typically based on polyethylene glycols commonly referred to as PEG and may include lesser amounts of glycerol, propylene glycol and water. Other hydrophilic materials used to a lesser extent include, but not limited to, methoxypolyethylene glycols, diethyleneglycol monoethyl ether tetrahyrofurfuryl alcohol polyethylene glycol, propylene carbonate, n-methyl-2-pyrrolidone, polyoxyethylene-poly-oxypropylene copolymers benzyl alcohol and ethyl alcohol.

The fill formulation may be prepared using established procedures employed for manufacture of pharmaceutical solutions, suspensions and semi-solids.

Individual or multiple liquid phases (if present) may be introduced into the capsule by means of a single, dual or multiple wedge design that facilitates in-situ capsule filling of multiple phases.

The liquid fill (if present) may include different liquid phases which are layered side-by-side in the softgel capsule. Each layered phase may incorporate an active ingredient or multiple active ingredients.

The fill materials may also include excipients known in the art of capsule encapsulation such as dispersants, surfactants, plasticizers, flavoring agents, opacifying agents, preservatives, embrittlement inhibiting agents, colorants, dyes and pigments, and disintegrants.

Typical immediate release coating films that may be used on the solid inclusions to be encapsulated in the capsule or on the shell of a capsule are hydro-alcoholic film coatings or cellulose film coating systems as used in various pharmaceutical solid oral dosage forms. Typical coating systems may be aqueous, alcohol or organic solvent based or combinations containing hydroxy-propyl-methyl cellulose and derivatives, and polyvinyl alcohol and derivatives. Examples of film coated dosage forms (e.g., tablets, beads, capsules) that could be used as the solid inclusions to be encapsulated include, without limitations, Amoxicillin, Azithromycin, Atenolol, Amlodipine, Acelofenac, Amtriptyline, Ampicillin HCl, Ciprofloxacin, Cefadroxil HCl, Celecoxib, Cimitidine, Calcium Tablets, Certizine HCl, Clarithromycin, Chloroquine Phosphate, Erythromycin estolate, Erythromycin striate, Enalpril Maleate, Elctronxib, Ferrous, fumarate, Famotidine, Flupenthixol, Fluoxetine Felodipine, Gatifloxacin, Gliclazide, Ibuprofen, lndapamide, Ketorolac, Ketoprofen, Levofixation, Levocetrinzie, Losartan, Potassium, Levamisole, Metormin, Methylopa, Metra+Tetraozole, Metronidozole, Methyl, Comblamine, Mefenamic acid, Metropralal Nifedipne, Norfloxacin, Nifedopine, Norfloxacin, Norflax+Tindazole, Oflaxacin, Oflaxacin+Omidazole, Olazzapine, Orridazole, Oflexacin+Omidazole Paracetamol, Pravastain, Prmethazine, Quinine, sulphate, Primaquine, Ramipril, Tindazole, Tiri+Doxicycline, Tiri+Tetracyline, Valdecoxib, Verapamil, herbal and Neutraceuticals.

Typical protective coatings that may be used on the solid inclusions to be encapsulated in the capsule or on the shell of a capsule may include, but are not limited to, polymer, antioxidants, chelating agents, colours or dyes.

Typical enteric coatings that may be used on the solid inclusions to be encapsulated in the capsule or on the shell of a capsule comprise, but are not limited to, one or more of the following recognized coating agents: methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate/alginic acid and stearic acid. Examples of enteric coated dosage forms (e.g., tablets, beads, capsules) include: Aspirin and Clopidogrel combination, Aspirin, Bisacodyl, Diclofenac-sodium, Doxylamine succinate, Esomeprazole, Garlic Tablets, Lansoprazole, Omeparazole, Pantoprazole, Pentoxyfilline, Pancreatin, Rabeprazole, Serratiopeptidase, and Sodium Valproate.

Sustained release solid inclusions and/or capsules may be film coated, enteric coated, or polymer matrix formulated. Sustained release film coatings may include, but are not limited to, a water insoluble material such as a wax or wax-like substance, fatty alcohols, shellac, zein, hydrogenated vegetable oils, water insoluble celluloses, polymers of acrylic and/or methacrylic acid, and any other slowly digestible or dispersible solids known in the art. Examples of sustained release dosage forms that could be used as the solid inclusions to be encapsulated include, without limitations: Acetazolamide Pellets, Aminophylline, Amitriptyline Pellets, Captoprill, Diclofenac Sodium, Diltiazem, Gliclazide, Iron, Levodopa, Lithium Carbonate, Metformin, Methyldopa, Nifedipine, Salbutamol Sulphate, Theophylline, Verapamil HCL, vitamin supplements, mineral supplements, and vitamins with Zinc.

Moisture shield coatings provide moisture barriers for moisture sensitive or hygroscopic drugs. Such coatings may be applied to solid inclusions to be encapsulated in a capsule or to the capsule itself to protect the solid inclusions and/or the capsule form moisture resulting from, for example, the encapsulation process (if it utilizes water as a processing aid). Examples of dosage forms incorporating moisture shield coatings that could be used as the solid inclusions to be encapsulated in the capsule include, but are not limited to: Amitriyptyline HCl, Amoxycillin and Clavulanic Acid combination, Atorvastatin and Calcium combination, Calcium Tablets, Clopidogrel, Ethambutol, Glucosamine and Chondritin combination, certain Herbal products, Multivitamins, Proton Pump Inhibitors Ranitidine HCl, Rifampicin and other moisture sensitive drugs.

Suitable active ingredients introduced in the solid inclusions to be encapsulated in the capsule and/or in a liquid fill (if present) and/or semi-solid fill (if present) may comprise APIs, nutritional supplements, substances used for therapeutic or cosmetic (e.g., non-pharmacologic action) purposes, functional excipients or combinations of active ingredients and functional excipients that control or otherwise affect the release of the active ingredient(s) into the gastrointestinal tract or site of absorption. If different phases are present in a capsule (e.g., a solid inclusion and a liquid fill or a semi-solid fill), each phase may contain one or more active ingredient(s). The active ingredient(s) in the different phases may be the same or different.

The present invention contemplates the use of any active ingredients known in the art. It is well within the knowledge of a skilled person in the art to select a particular combination of active ingredients or medicaments. In some embodiments, active ingredients may include, but are not limited to, the following: APIs, nutraceuticals, nutritional supplements, therapeutic substances, cosmetic ingredients (e.g., non-pharmacologic action) such as glycine and DHA, and functional excipients.

Suitable APIs may include, but are not limited to, the following: analgesics, anti-inflammatory agents, anti-helminthics, anti-arrhythmic agents, anti-asthma agents, anti-bacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-pyretics anti-thyroid agents, anti-tussives, anxiolytics, sedatives, hypnotics, neuroleptics, neuroprotective agents, beta-blockers, cardiac inotropic agents, cell adhesion inhibitors, corticosteroids, cytokine receptor activity modulators, diuretics, anti-Parkinson's agents, gastrointestinal agents, histamine H-receptor antagonists, HMG-CoA reductase inhibitors, keratolytics, lipid regulating agents, muscle relaxants, nitrates and other anti-anginal agents, non-steroid anti-asthma agents, nutritional agents, opioid analgesics, sex hormones, stimulants, and anti-erectile dysfunction agents.

Suitable nutraceuticals may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplements may include vitamins, minerals, fiber, fatty acids, amino acids, herbal supplements or a combination thereof.

Suitable vitamins may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplements may include, but are not limited to, the following: *arnica*, bilberry, black cohosh, cat's claw, chamomile, *echinacea*, evening primrose oil, fenugreek, flaxseed, feverfew, garlic, ginger root, ginko *biloba, ginseng*, goldenrod, hawthorn, kava-kava, licorice, milk thistle, *psyllium*, rauowolfia, *senna*, soybean, St. John's wort, saw palmetto, turmeric, valerian. Minerals may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

The present invention may reduce problems, such as time and expense, associated with combining two or more APIs into one dosage form. New combinations in one dosage form require development of new formulations and require pharmaceutical and clinical studies to demonstrate safety, efficacy and potency. The present invention provides the capability to incorporate more than one API into a unit dosage form utilizing established forms of the API or APIs that may be in liquid or solid phases. The present invention allows retention of the established tablet, caplet or capsule form of an API. This provides the capability to retain the pharmaceutical characteristics of the solid inclusion, optionally in combination with a liquid fill or semi-solid fill. Key characteristics include: physical and chemical stability, API release profile of the solid inclusion, bioavailability and clinical performance. Retention of the established clinical performance by incorporation of the original solid inclusion may avoid the need to conduct extensive Phase III clinical studies that would otherwise be required with a new formulation.

The present invention may permit the use of a smaller dosage form than those commercially sold. Encapsulation of a solid inclusion in a capsule provides protection against dissolution of the solid inclusion prior to reaching the intended target site. Thus, an encapsulated solid inclusions may not need to be as durable as compared to commercially available solid dosage forms. The present invention may reduce the need for excipients which function to prevent early dissolution of the solid inclusion when ingested, permitting the use of a smaller and cheaper solid dosage form. In typical softgel formulations that are designed to give a rapid onset by releasing the drug as a solution, the size of the capsule is proportional to the amount of API that can be dissolved in the formulation. By including a portion of the dose as a solid, and a portion as a solution, the rapid onset of action is preserved by the solution portion, and the dose is increased by the solid portion, thereby creating a smaller capsule for the same size dose that would otherwise be possible in a 100% solution formulation.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method comprising:
   introducing a continuous first film on a first rotating encapsulation die comprised of a first series of cavities;
   introducing a continuous second film on a second rotating encapsulation die comprised of a second series of cavities;
   wherein the first series of cavities and the second series of cavities are synchronized to align with each other as the first rotating encapsulation die and the second rotating encapsulation die turn, and wherein each cavity in the first series of cavities and in the second series of cavities forming one half of a total cavity for a capsule to be formed;
   mechanically dispensing at least one solid inclusion from a dispensing tube, the dispensing tube integrated into a wedge positioned between the continuous first film and the continuous second film of the first rotating encapsulation die and of the second rotating encapsulation die, respectively, the dispensing tube being positioned off-center in the wedge and aligned with a first row of cavities in the first rotating encapsulation die and a second row of cavities in the second rotating encapsulation die;
   trapping the at least one solid inclusion between the continuous first film, in a section of the continuous first film aligned over a die cavity, and the wedge to form a first half of a capsule within a cavity of the first rotating encapsulation die;
   rotating the first rotating encapsulation die and the second rotating encapsulation die in counter directions to contact the continuous first film and continuous second film between the first rotating encapsulation die and the second rotating encapsulation die to form a closed capsule; and
   simultaneously fusing a first pair of edges of the continuous first film and a second pair of edges of the continuous second film between the cavity of the first rotating encapsulation die and a cavity of the second rotating encapsulation die to hermetically seal the at least one solid inclusion into the closed capsule,
   wherein the mechanically dispensing at least one solid inclusion comprises:
   retracting a dispensing plunger in the dispensing tube, the dispensing tube being positioned adjacent to the feeding tube;
   transferring the at least one solid inclusion from the feeding tube into the dispensing tube through gravity;
   timing the dispensing plunger to eject the at least one solid inclusion from the dispensing tube with the rotation of the first rotating encapsulation die such that the at least one solid inclusion is trapped between the continuous first film and the wedge in the cavity of the first rotating encapsulation die to form a first half of a capsule; and
   ejecting the at least one solid inclusion.

2. The method of claim 1, further comprising mechanically dispensing a liquid through the wedge in synchrony with the rotating of the first rotating encapsulation die and of the second rotating encapsulation die to allow for timely trapping of the dispensed liquid with the at least one solid inclusion within the closed capsule.

3. The method of claim 1, wherein the mechanically dispensing at least one solid inclusion comprises:
   retracting an actuator positioned at a top of the dispensing tube to load a plurality of solid inclusions into the dispensing tube from a hopper holding a reservoir of solid inclusions;
   timing the actuator to extend and eject the at least one solid inclusion from the dispensing tube in synchrony with the rotation of the first rotating encapsulation die such that the at least one solid inclusion is trapped between the continuous first film and the wedge in the cavity of the first rotating encapsulation die to form a first half of a capsule;
   extending the actuator a distance equivalent to a number of solid inclusions to be placed in the capsule; and
   ejecting the number of solid inclusions to be placed in the capsule.

4. The method of claim 3, wherein the actuator is selected from the group consisting of electromagnetic, rotary screw driven, cam driven, hydraulically driven, and pneumatically driven.

5. The method of claim 1, wherein the mechanically dispensing further
   comprises filling liquid into the dispensing tube to displace air.

6. The method of claim 5, wherein the liquid is supplied from a liquid hopper such that the level of the liquid in the dispensing tube is equivalent to the level of the liquid in the hopper.

7. The method of claim 1, wherein the loading is continuous.

8. A system comprising:
a first rotating encapsulation die comprising a first set of die cavities;
a continuous first film on the first rotating encapsulation die;
a second rotating encapsulation die comprising a second set of die cavities;
a continuous second film on the second rotating encapsulation die;
a wedge positioned between the first rotating encapsulation die and the second rotating encapsulation die;
a dispensing tube integrated into the wedge and positioned off-center in the wedge and aligned with a first row of cavities in the first rotating encapsulation die and a second row of cavities in the second rotating encapsulation die for dispensing at least one solid inclusion; a mechanical dispensing mechanism and a synchronization mechanism for synchronizing the rotation of at least one of the first rotating encapsulation die or the second rotating encapsulation die with the mechanical dispensing of the at least one solid inclusion such that the at least one solid inclusion is timely trapped between the continuous first film and the wedge in a cavity within the first set of die cavities to form a first half of a capsule; and
a dispensing tube integrated into the wedge and positioned adjacent to a feeding tube, the dispensing tube comprising a dispensing plunger for controlling the number of solid inclusions dispensed from the feeding tube into the dispensing tube through gravity.

9. The system of claim 8, wherein the mechanical dispensing mechanism comprises an actuator positioned at a top of the dispensing tube for loading the dispensing tube and ejecting the at least one solid inclusion in synchrony with the rotation of at least one of the first rotating encapsulation die or the second rotating encapsulation die such that the at least one solid inclusion gets trapped between at least one of the continuous first film or the continuous second film and the wedge in a cavity within at least one of the first set of die cavities or the second set of die cavities to form a first half of a capsule.

10. The system of claim 9, wherein the actuator is selected from the group consisting of electromagnetic, rotary screw driven, cam driven, hydraulically driven, and pneumatically driven.

11. The system of claim 1, further comprising a liquid hopper for supplying liquid to the dispensing tube to displace air upon ejection of the at least one solid inclusion.

12. The system of claim 8, wherein the dispensing tube further comprises liquid above the plurality of solid inclusions, wherein the dispensing tube is connected to the mechanical dispensing mechanism, the mechanical dispensing mechanism being a pump for dispensing the at least one solid inclusion in synchrony with the rotation of at least one of the first rotating encapsulation die or the second rotating encapsulation die such that the at least one solid inclusion gets trapped between at least one of the continuous first film or the continuous second film and the wedge in a cavity within at least one of the first set of die cavities or the second set of die cavities to form a first half of a capsule.

13. The system of claim 12, wherein the pump is a positive displacement pump.

14. The system of claim 1, further comprising a liquid fill or a semi-solid fill dispensing tube integrated into a center of the wedge for mechanically dispensing and filling the capsule with the liquid fill or the semi-solid fill in synchrony with the rotation of at least one of the first rotating encapsulation die or the second rotating encapsulation die to allow for timely trapping of the dispensed liquid fill or the dispensed semi-solid fill with the at least one solid inclusion within the capsule.

15. The system of claim 1, wherein the at least one solid inclusion is selected from the group consisting of beads, tablets, capsules, caplets, pellets, granules, and combinations thereof.

16. The system of claim 1, wherein the at least one solid inclusion has a shape selected from the group consisting of round, oval, oblong, and spherical.

\* \* \* \* \*